US012622913B2

(12) United States Patent
Ulmann et al.

(10) Patent No.: US 12,622,913 B2
(45) Date of Patent: May 12, 2026

(54) FOLATE SALTS FOR MEDICAL USE

(71) Applicant: APROFOL AG, Appenzell Steinegg (CH)

(72) Inventors: Martin Ulmann, Dachsen (CH); Gerd Wiesler, Lohn (CH); Arthur Bodenmüller, Seltisberg (CH); Markus Müller, Wegenstetten (CH)

(73) Assignee: APROFOL AG (CH)

( * ) Notice: Subject to any disclaimer, the term of this patent is extended or adjusted under 35 U.S.C. 154(b) by 306 days.

(21) Appl. No.: 18/316,730

(22) Filed: May 12, 2023

(65) Prior Publication Data

US 2023/0277544 A1 Sep. 7, 2023

Related U.S. Application Data

(63) Continuation of application No. 16/651,688, filed as application No. PCT/EP2018/073280 on Aug. 29, 2018, now Pat. No. 11,690,846.

(51) Int. Cl.
*A61K 31/519* (2006.01)
*A61K 31/53* (2006.01)

(52) U.S. Cl.
CPC ............ *A61K 31/519* (2013.01); *A61K 31/53* (2013.01)

(58) Field of Classification Search
CPC .... A61K 31/519; A61K 31/53; C07D 475/04; A61P 3/00; A61P 25/00; A61P 35/00
See application file for complete search history.

(56) References Cited

U.S. PATENT DOCUMENTS

| | | | | |
|---|---|---|---|---|
| 11,690,846 B2 * | 7/2023 | Ulmann | ............... | A61K 31/519 514/249 |
| 12,048,702 B2 * | 7/2024 | Ulmann | ................. | A61K 31/51 |
| 2002/0052374 A1 | 5/2002 | Rabelink et al. | | |
| 2010/0105691 A1 | 4/2010 | Me et al. | | |
| 2013/0118989 A1 | 5/2013 | Caires et al. | | |
| 2016/0207925 A1 | 7/2016 | Fracchia | | |

FOREIGN PATENT DOCUMENTS

| | | | |
|---|---|---|---|
| CN | 107304212 | A | 10/2017 |
| DE | 2063027 | A1 | 7/1971 |
| JP | 47-19917 | U | 11/1972 |
| JP | H03128380 | A | 5/1991 |
| JP | 2004-59475 | A | 2/2004 |
| JP | 2014-533268 | A | 12/2014 |
| WO | 1993017022 | A1 | 9/1993 |
| WO | 2006119589 | A2 | 11/2006 |
| WO | 2009103334 | A1 | 8/2009 |
| WO | 2020002714 | A1 | 1/2020 |

* cited by examiner

*Primary Examiner* — Sarah Pihonak
(74) *Attorney, Agent, or Firm* — NGUYEN TARBET IP LAW

(57) ABSTRACT

The invention relates to amorphous folate salt. The salt consists of a folate anion and an organic cation. The folate anion is selected from the group consisting of 5-formyl-(6S)-tetrahydrofolic acid, 10-formyl-(6R)-tetrahydrofolic acid, 5-methyl-(6S)-tetrahydrofolic acid, (6S)-tetrahydrofolic acid, 5,10-Methylene-(6R)-tetrahydrofolic acid, and its oxidized derivatives JK12A and Mefox, and the cation is an organic compound selected from the group arginine, choline, acetylcholine, 1,1-dimethyl-biguanidin phenylethyl-biguanidin, betaine-methylester and dimethylaminoethanol. The cation is an organic compound with a complementary pharmacological activity.

5 Claims, No Drawings

FOLATE SALTS FOR MEDICAL USE

CROSS REFERENCE

This application is a Continuation and claims benefit of U.S. patent application Ser. No. 16/651,688 filed Mar. 27, 2020, which is a 371 application and claims benefit of International Patent Application No. PCT/EP2018/073280 filed Aug. 29, 2018, which claims benefit of European Patent Application No. 17020449.9 filed Sep. 29, 2017, the specification(s) of which is/are incorporated herein in their entirety by reference.

FIELD OF THE INVENTION

The present invention relates to folate salts, their preparation and compositions comprising the same.

BACKGROUND OF THE INVENTION

Depression and other mental health disorders such as dementia, autism, ADHD and Alzheimer, as well as chronic non-communicable diseases (NCDs) such as diabetes 2, vascular diseases, and cancer are a growing burden for patients and the health care systems, especially in view of the aging population. There are various reasons for these different diseases; however, as a common risk factor a suboptimal folate-status has been found, in the whole body or in specific tissues.

It is well known that vitamins of the B-complex group are involved in numerous metabolic processes of the body, e.g. in the conversion of carbohydrates into glucose, which is metabolized to produce energy. These vitamins are further essential in the breakdown of fats and proteins and play an important role in maintaining muscle tone along the lining of the digestive tract and promoting health of the nervous system, and e.g. eyes, skin, hair, liver.

In addition, it is known that folate is compulsory in the production and maintenance of new cells. Especially important in times of rapid cell division and growth such as infancy and pregnancy. Folate is needed to replicate DNA. Thus, folate deficiency hinders DNA synthesis and cell division, affecting most clinically the bone marrow, a site of rapid cell turnover. Because RNA and protein synthesis are not hindered, large red blood cells, i.e. megaloblasts, are produced, resulting in macrocytic anemia, such as megaloblastic anemia, as may be seen in celiac disease, and in anemias of nutritional origin, or in pregnancy, infancy, or childhood. Accordingly, both adults, especially elderly, and children need folate to make normal red blood cells and prevent anemia. Folate also helps prevent changes to DNA that may lead to cancer.

Folate derivatives such as diverse tetrahydrofolic acid derivatives may also be used as drug or as basic substance for the preparation of other derivatives. Yet, also tetrahydrofolic acid and the derivatives thereof are known to possess an extreme instability, particularly due to their susceptibility to oxidation. In particular, 5-formyltetrahydrofolic acid (Folinic acid, Leucovorin) has importance as a drug ingredient mainly in oncology, as concomitant therapy with methotrexate and 5-fluorouracil treatment, and in the treatment of folic acid deficiency anemia associated with pregnancy, antibiotic therapy etc. Among folates and reduced folates, the calcium salts can be mentioned as the most relatively stable derivatives: U.S. Pat. Nos. 5,817,659 and 6,441,168 disclose crystalline salts, preferably calcium salts, of 5-methyl-(6R, S)-, (6S)- or (6R)-tetrahydrofolic acid having a water of crystallization of at least one equivalent per equivalent of said acid. 5-methyltetrahydrofolate is the only folic acid derivative on the market which can directly penetrate the blood/brain barrier without further metabolism. Naturally occurring 5-methyltetrahydrofolic acid is solely in the S form; the R form is considered biochemically inactive and is excreted through the kidney. Besides, several compositions for human and animal consumption, comprising either folates and/or reduced folates, have been reported, in various forms and together with vitamins, arginine, lysine, thiamine and/or other active ingredients, either as a nutritional supplement or for the treatment and prevention of various diseases such as, for instance, neurological, pathophysiological, cardiovascular diseases, arthritic and inflammation conditions.

Various folate salts are known. In general, these salts comprise a folate and an inorganic cation such as calcium and magnesium or an organic cation such as glucosamine or galactosamine. These alkaline earth metal cations are inert insofar that they themselves do not show any pharmacological effect in humans. The scarce solubility in aqueous solutions of such salts has been widely reported. WO 2009/103334 describes a 5-methyl-tetrahydrofolic acid glucosamine salt (5-MTHF-glucosamine) having a good water solubility. Further, the solubility of folate salts in apolar solvents is very limited as well. For instance, the 5-MTHF-glucosamine was described as a creamy to light-brown powder that is very soluble in water (at 25° C.), soluble in dilute acid or dilute alkali and insoluble in organic solvents (EFSA Journal 2013; 11(10):3358). Aqueous compositions with improved solubility and stability of folates have been disclosed, e.g. in U.S. Pat. Nos. 9,301,922 and 9,642,853. In addition, numerous compositions of folates comprising folates and further compounds such as vitamins, lysine, thiamin and other active ingredients have been described. However, stable salts of folates with good solubility in water and apolar solvents combining a further active compound would allow more versatile pharmaceutical compositions.

SUMMARY OF THE INVENTION

The object of the present invention is to provide folate salts combining a further active compound and showing a good stability, a high solubility in apolar solvents and good water-solubility.

The object is achieved by a folate salt according to the present invention as defined in claim 1. Further preferred embodiments are subject to the dependent claims.

An amorphous folate salt according to the present invention consists of a tetrahydrofolic acid anion and an organic cation, whereby the anion is selected from the group consisting of 5-formyl-(6S)-tetrahydrofolic acid, 10-formyl-(6R)-tetrahydrofolic acid, 5-methyl-(6S)-tetrahydrofolic acid, (6S)-tetrahydrofolic acid, 5,10-diformyl-(6S)-tetrahydrofolic acid, 5-methyl-10-formyl-(6S)-tetrahydrofolic acid, 5,10-Methylene-(6R)-tetrahydrofolic acid, and its oxidized derivatives JK12A and Mefox. Further the cation is an organic compound which is selected from the group arginine, choline, acetylcholine, 1,1-dimethyl-biguanidin, phenylethylbiguanidin, betaine-methylester and dimethylaminoethanol. The folate salts have a high solubility in an apolar solvent, said apolar solvent having a relative polarity of 0.82 compared to water.

As a high solubility in an apolar solvent is considered a solubility of higher than 5 mass-percent (m/m) of a particular folate salt in a particular apolar solvent. Solubility has been determined at 20° C.

The structures of Mefox is shown below:

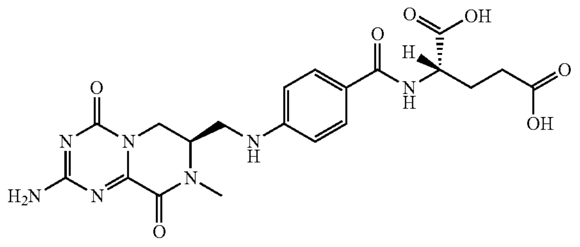 [SMILES: CN1C(=O)c2nc(N)nc(=O)n2C[C@H]1CNc1ccc(C(=O)N[C@@H](CCC(=O)O)C(=O)O)cc1]

The structure of JK12A is shown below:

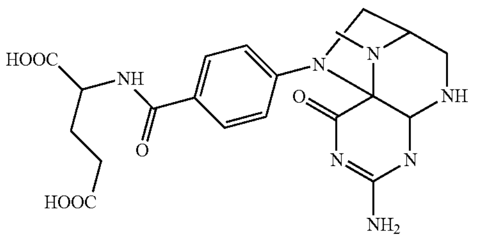 [SMILES: CN1C2CNC3NC(N)=NC(=O)C31N(c1ccc(C(=O)NC(CCC(=O)O)C(=O)O)cc1)C2]

Both compounds, Mefox and JK12A are oxidized derivatives of 5-methyl-(6S)-tetrahydrofolic acid.

DESCRIPTION OF PREFERRED EMBODIMENTS

In a preferred embodiment, the amorphous folate salt consists of tetrahydrofolic acid anion and an organic cation. The anion is selected from the group consisting of 5-formyl-(6S)-tetrahydrofolic acid, 10-Formyl-(6R)-tetrahydrofolic acid, 5-methyl-(6S)-tetrahydrofolic acid, (6S)-tetrahydrofolic acid, 5,10-Methylene-(6R)-tetrahydrofolic acid and its oxidized derivatives JK12A and Mefox. The cation is selected from the group consisting of di-arginine, di-choline, di-acetylcholine, di-(1,1-dimethyl-biguanidin), di-(phenylethyl-biguanidin), di-betaine-methylester, and di-dimethyl-amino-ethanol.

In another embodiment, the amorphous folate salt consists of tetrahydrofolic acid anion and an organic cation, whereby the anion is selected from the group consisting of 5-formyl-(6S)-tetrahydrofolic acid, 10-Formyl-(6R)-tetrahydrofolic acid, 5-methyl-(6S)-tetrahydrofolic acid, (6S)-tetrahydrofolic acid, 5,10-Methylene-(6R)-tetrahydrofolic acid and its oxidized derivatives JK12A and Mefox, and whereby the cation is selected from the group consisting of mono-arginine, mono-choline, mono-acetylcholine, mono-(1,1-dimethyl-biguanidin), mono-(phenylethyl-biguanidin)), mono-betaine-methylester, and mono-dimethyl-amino-ethanol.

In a further embodiment, the amorphous tetrahydrofolic acid salt consists of the tetrahydrofolic acid anion is 5-formyl-(6S)-tetrahydrofolic acid and the organic cation is mono-arginine wherein the $^1$H-NMR shifts in $D_2O$ are

| δ (1H) in ppm | Multiplicity | Intensity |
|---|---|---|
| 7.59 | d | 2H |
| 6.67 | d | 2H |
| 4.25 | m | 1H |

-continued

| δ (1H) in ppm | Multiplicity | Intensity |
|---|---|---|
| 3.69 | t | 1H |
| 3.58 | m | 1H |
| 3.41 | m | 2H |
| 3.19 | m | 5H |
| 2.71 | s | 3H |
| 2.27 | m | 2H |
| 2.10 | m | 1H |
| 1.96 | m | 1H |
| 1.83 | m | 2H |
| 1.60 | m | 2H |

In a further embodiment, the amorphous tetrahydrofolic acid salt consists of the tetrahydrofolic acid anion is 5-formyl-(6S)-tetrahydrofolic acid and the organic cation is mono-(1,1-dimethyl-biguanidine) wherein the $^1$H-NMR shifts in $D_2O$ are

| δ (1H) in ppm | Multiplicity | Intensity |
|---|---|---|
| 8.51/7.8 | s/s | 1H |
| 7.54/7.50 | d/d | 2H |
| 6.62/6.57 | d/d | 2H |
| 4.73 | m | 1H |
| 4.27 | m | 1H |
| 3.42 | m | 1H |
| 3.28 | m | 2H |
| 3.16 | m | 1H |
| 2.92 | s | 6H |
| 2.32 | m | 2H |
| 2.12 | m | 1H |
| 1.95 | m | 1H |

In a further embodiment, the amorphous tetrahydrofolic acid salt consists of the tetrahydrofolic acid anion is 5-formyl-(6S)-tetrahydrofolic acid and the organic cation is mono-(phenylethyl-biguanidine) wherein the $^1$H-NMR shifts in $D_2O$ are

| δ (1H) in ppm | Multiplicity | Intensity |
|---|---|---|
| 8.50/7.80 | s/s | 1H |
| 7.54/7.50 | d/d | 2H |
| 7.27 | m | 2H |
| 7.19 | m | 3H |
| 6.62/6.57 | d/d | 2H |
| 4.75 | m | 1H |
| 4.29 | m | 1H |
| 3.40 | m | 1H |
| 3.38 | m | 2H |
| 3.26 | m | 2H |
| 3.15 | m | 1H |
| 2.76 | m | 2H |
| 2.33 | m | 2H |
| 2.13 | m | 1H |
| 1.96 | m | 1H |

In a further embodiment, the amorphous tetrahydrofolic acid salt consists of the tetrahydrofolic acid anion is 5-formyl-(6S)-tetrahydrofolic acid and the organic cation is mono-choline wherein the $^1$H-NMR shifts in $D_2O$ are

| δ (1H) in ppm | Multiplicity | Intensity |
|---|---|---|
| 8.50/7.80 | s/s | 1H |
| 7.54/7.50 | d/d | 2H |
| 6.62/6.57 | d/d | 2H |
| 4.73 | m | 1H |

-continued

| δ (1H) in ppm | Multiplicity | Intensity |
|---|---|---|
| 4.27 | m | 1H |
| 3.93 | m | 2H |
| 3.43 | m | 1H |
| 3.39 | m | 2H |
| 3.27 | m | 2H |
| 3.16 | m | 1H |
| 3.07 | s | 9H |
| 2.32 | m | 2H |
| 2.12 | m | 1H |
| 1.95 | m | 1H |

In a further embodiment, the amorphous tetrahydrofolic acid salt consists of the tetrahydrofolic acid anion is 5-methyl-(6S)-tetrahydrofolic acid and the organic cation is mono-(1,1-dimethyl-biguanidine) wherein the $^1$H-NMR shifts in $D_2O$ are

| δ (1H) in ppm | Multiplicity | Intensity |
|---|---|---|
| 7.59 | d | 2H |
| 6.67 | d | 2H |
| 4.25 | m | 1H |
| 3.57 | m | 1H |
| 3.38 | m | 2H |
| 3.20 | m | 1H |
| 3.13 | m | 1H |
| 2.95 | s | 6H |
| 2.84 | m | 1H |
| 2.67 | s | 3H |
| 2.26 | m | 2H |
| 2.10 | m | 1H |
| 1.96 | m | 1H |

In a further embodiment, the amorphous tetrahydrofolic acid salt consists of the tetrahydrofolic acid anion is 5-methyl-(6S)-tetrahydrofolic acid and the organic cation is mono-(phenylethyl-biguanidine) wherein the $^1$H-NMR shifts in $D_2O$ are

| δ (1H) in ppm | Multiplicity | Intensity |
|---|---|---|
| 7.56 | d | 2H |
| 7.27 | m | 2H |
| 7.19 | m | 3H |
| 6.63 | d | 2H |
| 4.23 | m | 1H |
| 3.53 | m | 1H |
| 3.38 | m | 2H |
| 3.35 | m | 2H |
| 3.12 | m | 1H |
| 3.07 | m | 1H |
| 2.76 | m | 2H |
| 2.64 | s | 3H |
| 2.25 | m | 2H |
| 2.09 | m | 1H |
| 1.96 | m | 1H |

In a further embodiment, the amorphous tetrahydrofolic acid salt consists of the tetrahydrofolic acid anion is 5-methyl-(6S)-tetrahydrofolic acid and the organic cation is mono-choline wherein the $^1$H-NMR shifts in $D_2O$ are

| δ (1H) in ppm | Multiplicity | Intensity |
|---|---|---|
| 7.56 | d | 2H |
| 6.65 | d | 2H |
| 4.20 | m | 1H |

-continued

| δ (1H) in ppm | Multiplicity | Intensity |
|---|---|---|
| 3.95 | m | 2H |
| 3.43 | m | 1H |
| 3.40 | t | 2H |
| 3.20 | d | 1H |
| 3.08 | s | 9H |
| 3.04 | m | 1H |
| 2.99 | m | 1H |
| 2.89 | m | 1H |
| 2.42 | s | 3H |
| 2.20 | m | 2H |
| 2.04 | m | 1H |
| 1.91 | m | 1H |

In a further embodiment, the amorphous tetrahydrofolic acid salt consists of the tetrahydrofolic acid anion is 5-formyl-(6S)-tetrahydrofolic acid and the organic cation is mono-2-dimethylaminoethanol wherein the $^1$H-NMR shifts in $D_2O$ are

| δ (1H) in ppm | Multiplicity | Intensity |
|---|---|---|
| 8.58/7.87 | s/s | 1H |
| 7.61/7.57 | d/d | 2H |
| 6.69/6.64 | d/d | 2H |
| 4.81 | m | 1H |
| 4.33 | m | 1H |
| 3.85 | t | 2H |
| 3.50 | m | 1H |
| 3.34 | m | 2H |
| 3.24 | t | 2H |
| 3.22 | m | 1H |
| 2.87 | S | 6H |
| 2.38 | m | 2H |
| 2.17 | m | 1H |
| 2.01 | m | 1H |

In a further embodiment, the amorphous tetrahydrofolic acid salt consists of the tetrahydrofolic acid anion is 5-methyl-(6S)-tetrahydrofolic acid and the organic cation is mono-arginine wherein the $^1$H-NMR shifts in $D_2O$ are

| δ (1H) in ppm | Multiplicity | Intensity |
|---|---|---|
| 7.59 | d | 2H |
| 6.67 | d | 2H |
| 4.25 | m | 1H |
| 3.69 | t | 1H |
| 3.58 | m | 1H |
| 3.41 | m | 2H |
| 3.19 | m | 5H |
| 2.71 | s | 3H |
| 2.27 | m | 2H |
| 2.10 | m | 1H |
| 1.96 | m | 1H |
| 1.83 | m | 2H |
| 1.60 | m | 2H |

In a further embodiment, the amorphous tetrahydrofolic acid salt consists of the tetrahydrofolic acid anion is 5-formyl-(6S)-tetrahydrofolic acid and the organic cation is mono-acetylcholine wherein the $^1$H-NMR shifts in $D_2O$ are

| δ (1H) in ppm | Multiplicity | Intensity |
|---|---|---|
| 8.58/7.86 | s/s | 1H |
| 7.61/7.58 | d/d | 2H |
| 6.69/6.64 | d/d | 2H |
| 4.81 | m | 1H |

-continued

| δ (1H) in ppm | Multiplicity | Intensity |
|---|---|---|
| 4.49 | m | 2H |
| 4.26 | m | 1H |
| 3.67 | m | 2H |
| 3.50 | m | 1H |
| 3.57 | m | 2H |
| 3.25 | m | 1H |
| 3.15 | s | 9H |
| 2.25 | m | 2H |
| 2.10 | m | 1H |
| 2.08 | s | 3H |
| 1.97 | m | 1H |

In a further embodiment, the amorphous tetrahydrofolic acid salt consists of the tetrahydrofolic acid anion is 5-methyl-(6S)-tetrahydrofolic acid and the organic cation is mono-acetyicholine wherein the $^1$H-NMR shifts in $D_2O$ are

| δ (1H) in ppm | Multiplicity | Intensity |
|---|---|---|
| 7.61 | d | 2H |
| 6.69 | d | 2H |
| 4.48 | m | 2H |
| 4.26 | m | 1H |
| 3.66 | m | 2H |
| 3.45 | dd | 1H |
| 3.25 | m | 1H |
| 3.15 | s | 9H |
| 3.09 | m | 1H |
| 3.03 | m | 1H |
| 2.93 | m | 1H |
| 2.48 | s | 3H |
| 2.25 | m | 2H |
| 2.11 | m | 1H |
| 2.08 | s | 3H |
| 1.97 | m | 1H |

In a further embodiment, the amorphous tetrahydrofolic acid salt consists of the tetrahydrofolic acid anion is 5-formyl-(6S)-tetrahydrofolic acid and the organic cation is di-arginine wherein the $^1$H-NMR shifts in $D_2O$ are

| δ (1H) in ppm | Multiplicity | Intensity |
|---|---|---|
| 8.53/7.82 | s/s | 1H |
| 7.56/7.53 | d/d | 2H |
| 6.64/6.59 | d/d | 2H |
| 4.75 | m | 1H |
| 4.21 | m | 1H |
| 3.66 | t | 2H |
| 3.44 | m | 1H |
| 3.30 | m | 2H |
| 3.17 | m | 1H |
| 3.11 | S | 4H |
| 2.23 | m | 2H |
| 2.07 | m | 1H |
| 1.95 | m | 1H |
| 1.79 | m | 4H |
| 1.58 | m | 4H |

In a further embodiment, the amorphous folate salt consists of the tetrahydrofolic acid anion is 5-formyl-(6S)-tetrahydrofolic acid and the organic cation is di-choline, wherein the $^1$H-NMR shifts in $D_2O$ are

| δ (1H) in ppm | Multiplicity | Intensity |
|---|---|---|
| 8.60/7.88 | s/s | 1H |
| 7.63/7.59 | d/d | 2H |

-continued

| δ (1H) in ppm | Multiplicity | Intensity |
|---|---|---|
| 6.71/6.66 | d/d | 2H |
| 4.83 | m | 1H |
| 4.27 | m | 1H |
| 4.01 | m | 4H |
| 3.48 | m | 1H |
| 3.47 | m | 4H |
| 3.37 | m | 2H |
| 3.27 | m | 1H |
| 3.14 | S | 18H |
| 2.26 | m | 2H |
| 2.11 | m | 1H |
| 1.98 | m | 1H |

In another embodiment, the amorphous folate salt consists of the tetrahydrofolic acid anion is 5-formyl-(6S)-tetrahydrofolic acid and the organic cation is di-(1,1-dimethyl-biguanidin) whereby the $^1$H-NMR shifts in $D_2O$ are

| δ (1H) in ppm | Multiplicity | Intensity |
|---|---|---|
| 8.57/7.86 | s/s | 1H |
| 7.60/7.56 | d/d | 2H |
| 6.68/6.63 | d/d | 2H |
| 4.80 | m | 1H |
| 4.25 | m | 1H |
| 3.48 | m | 1H |
| 3.33 | m | 2H |
| 3.22 | m | 1H |
| 2.96 | s | 12H |
| 2.25 | m | 2H |
| 2.10 | m | 1H |
| 1.96 | m | 1H |

In a further embodiment, the amorphous folate salt consists of the tetrahydrofolic acid anion is 5-formyl-(6S)-tetrahydrofolic acid and the organic cation is di-(phenyl-ethyl-biguanidin) wherein the $^1$H-NMR shifts in $D_2O$ are

| δ (1H) in ppm | Multiplicity | Intensity |
|---|---|---|
| 8.52/7.84 | s/s | 1H |
| 7.60/7.56 | d/d | 2H |
| 7.31 | m | 4H |
| 7.23 | m | 6H |
| 6.67/6.61 | d/d | 2H |
| 4.77 | m | 1H |
| 4.26/4.22 | m | 1H |
| 3.48 | m | 1H |
| 3.42 | m | 4H |
| 3.28 | m | 2H |
| 3.16 | m | 1H |
| 2.79 | m | 4H |
| 2.26 | m | 2H |
| 2.10 | m | 1H |
| 1.96 | m | 1H |

In another embodiment, the amorphous folate salt consists of the tetrahydrofolic acid anion is 5-methyl-(6S)-tetrahydrofolic acid and the organic cation is di-arginine, wherein the $^1$H-NMR shifts in $D_2O$ are

| δ (1H) in ppm | Multiplicity | Intensity |
|---|---|---|
| 7.62 | d | 2H |
| 6.70 | d | 2H |
| 4.27 | m | 1H |
| 3.72 | t | 2H |
| 3.48 | m | 1H |

-continued

| δ (1H) in ppm | Multiplicity | Intensity |
|---|---|---|
| 3.28 | m | 1H |
| 3.18 | t | 4H |
| 3.15 | m | 1H |
| 3.07 | m | 1H |
| 2.98 | m | 1H |
| 2.53 | s | 3H |
| 2.28 | m | 2H |
| 2.12 | m | 1H |
| 1.99 | m | 1H |
| 1.86 | m | 4H |
| 1.64 | m | 4H |

In another embodiment, the amorphous folate salt consists of the tetrahydrofolic acid anion is 5-methyl-(6S)-tetrahydrofolic acid and the organic cation is di-(1,1-dimethyl-biguanidin), wherein the $^1$H-NMR shifts in $D_2O$ are

| δ (1H) in ppm | Multiplicity | Intensity |
|---|---|---|
| 7.59 | d | 2H |
| 6.67 | d | 2H |
| 4.25 | m | 1H |
| 3.44 | m | 1H |
| 3.24 | m | 1H |
| 3.10 | m | 1H |
| 3.01 | m | 1H |
| 2.95 | s | 12H |
| 2.92 | m | 1H |
| 2.48 | s | 3H |
| 2.25 | m | 2H |
| 2.10 | m | 1H |
| 1.97 | m | 1H |

In a further embodiment, the amorphous folate salt consists of the tetrahydrofolic acid anion is 5-methyl-(6S)-tetrahydrofolic acid and the organic cation is di-(phenyl-ethyl-biguanidin), wherein the $^1$H-NMR shifts in $D_2O$ are

| δ (1H) in ppm | Multiplicity | Intensity |
|---|---|---|
| 7.58 | d | 2H |
| 7.29 | m | 4H |
| 7.21 | m | 6H |
| 6.65 | d | 2H |
| 4.24 | m | 1H |
| 3.44 | m | 1H |
| 3.40 | m | 4H |
| 3.24 | m | 1H |
| 3.10 | m | 1H |
| 3.01 | m | 1H |
| 2.91 | m | 1H |
| 2.78 | m | 4H |
| 2.49 | s | 3H |
| 2.24 | m | 2H |
| 2.09 | m | 1H |
| 1.96 | m | 1H |

In a further preferred embodiment, a pharmaceutical composition comprises at least one folate salt according to the present invention as the main active compound. The composition further comprises at least a pharmaceutically acceptable excipient. The composition may for instance comprise a buffer compound. Suitable and preferred buffer compounds are trometamol and HEPES. Further, an anti-oxidant compound may be present in the composition. Preferred antioxidant compounds are thioglycerol, dithiothreitol (DTT) and cysteine.

Further, at least one folate salt according to the present invention is used for the preparation of a medicament, a food additive or a nutritional supplement, for the prevention and/or treatment of either deficiencies or disorders that are positively affected by the administration of folate salt. There are a number of disease conditions which are positively influenced by compositions comprising folate salts. Such diseases are for instance pathophysiological, neurological and inflammatory diseases.

In addition, a method for preparing the amorphous folate salt according to the present invention, said tetrahydrofolic acid salt consisting of a folate acid anion and an organic cation, comprises the step of adding oxalic acid or alternatively a fluoride salt to an aqueous composition of folate acid earth alkaline metal salts.

EXAMPLES

Example 1

Preparation of 5-formyl-(6S)-tetrahydrofolic acid di L-arginine salt 10.0 g (16.62 mmol) of calcium levofolinate pentahydrate under argon was dissolved in 230 ml water at 70° C. Then 5.79 g (33.24 mmol) L-arginine was added, followed by 2.09 g (16.62 mmol) oxalic acid di-hydrate. After cooling to room temperature (RT), the precipitated calcium oxalate was filtered off through a Hyflo pad and the resulting clear solution (pH 6) evaporated to dryness. The crude product was then thoroughly digested with methanol, filtered and dried under vacuum at 60° C., to give 13.63 g of the title compound. Analytical data:

| δ (1H) in ppm | Multiplicity | Intensity |
|---|---|---|
| 8.53/7.82 | s/s | 1H |
| 7.56/7.53 | d/d | 2H |
| 6.64/6.59 | d/d | 2H |
| 4.75 | m | 1H |
| 4.21 | m | 1H |
| 3.66 | t | 2H |
| 3.44 | m | 1H |
| 3.30 | m | 2H |
| 3.17 | m | 1H |
| 3.11 | S | 4H |
| 2.23 | m | 2H |
| 2.07 | m | 1H |
| 1.95 | m | 1H |
| 1.79 | m | 4H |
| 1.58 | m | 4H |

Optical rotation: $\alpha^{20D}$ + 1.75° (c = 1 $H_2O$)

Example 2

Preparation of 5-formyl-(6S)-tetrahydrofolic acid di metformin salt 1.86 g (3.09 mmol) of calcium levofolinate pentahydrate under argon was dissolved in 43 ml Water at 70° C. Then 0.80 g (6.18 mmol) metformin free base was added, followed by 0.39 g (3.09 mmol) oxalic acid di-hydrate. After cooling to RT, the precipitated calcium oxalate was filtered off through a Hyflo pad and the resulting clear solution (pH 6) evaporated to dryness. The crude product was then thoroughly digested with ethanol, filtered and dried under vacuum at 60° C., to give 2.13 g of the title compound. Analytical data:

| δ (1H) in ppm | Multiplicity | Intensity |
|---|---|---|
| 8.57/7.86 | s/s | 1H |
| 7.60/7.56 | d/d | 2H |
| 6.68/6.63 | d/d | 2H |
| 4.80 | m | 1H |
| 4.25 | m | 1H |
| 3.48 | m | 1H |
| 3.33 | m | 2H |
| 3.22 | m | 1H |
| 2.96 | S | 12H |
| 2.25 | m | 2H |
| 2.10 | m | 1H |
| 1.96 | m | 1H |

Optical rotation: $\alpha^{20D}$ − 2.84° (c = 1 $H_2O$)

Example 3

Preparation of 5-formyl-(6S)-tetrahydrofolic acid di-phenformin salt 1.21 g (2.02 mmol) of calcium levofolinate pentahydrate under argon was dissolved in 43 ml water at 70° C. Then 0.83 g (4.04 mmol) phenformin free base was added, followed by 0.25 g (2.02 mmol) oxalic acid di-hydrate. After cooling to RT, the precipitated calcium oxalate was filtered off through a Hyflo pad and the resulting clear solution (pH 5.5) evaporated to dryness. The crude product was then thoroughly digested with acetonitrile, filtered and dried under vacuum at 60° C., to give 1.80 g of the title compound. Analytical data:

| δ (1H) in ppm | Multiplicity | Intensity |
|---|---|---|
| 8.52/7.84 | s/s | 1H |
| 7.60/7.56 | d/d | 2H |
| 7.31 | m | 4H |
| 7.23 | m | 6H |
| 6.67/6.61 | d/d | 2H |
| 4.77 | m | 1H |
| 4.26/4.22 | m | 1H |
| 3.48 | m | 1H |
| 3.42 | m | 4H |
| 3.28 | m | 2H |
| 3.16 | m | 1H |
| 2.79 | m | 4H |
| 2.26 | m | 2H |
| 2.10 | m | 1H |
| 1.96 | m | 1H |

Optical rotation: $\alpha^{20D}$ + 1.39° (c = 1 $H_2O$)

Example 4

Preparation of 5-Formyl-(6S)-tetrahydrofolic acid di-choline salt 1.92 g (3.19 mmol) of calcium levofolinate pentahydrate under argon was dissolved in 40 ml Water at 70° C. Then a filtered, aqueous solution of 0.79 g (6.38 mmol) choline fluoride (obtained from choline chloride and silver fluoride) was added. After cooling to 0° C., the precipitated calcium fluoride was filtered off through a Hyflo pad and the resulting clear solution (pH 6.5) evaporated to dryness. The crude product was then thoroughly digested with acetonitrile, filtered and dried under vacuum at 60° C., to give 1.89 g of the title compound. Analytical data:

| δ (1H) in ppm | Multiplicity | Intensity |
|---|---|---|
| 8.60/7.88 | s/s | 1H |
| 7.63/7.59 | d/d | 2H |
| 6.71/6.66 | d/d | 2H |
| 4.83 | m | 1H |
| 4.27 | m | 1H |
| 4.01 | m | 4H |
| 3.48 | m | 1H |
| 3.47 | m | 4H |
| 3.37 | m | 2H |
| 3.27 | m | 1H |
| 3.14 | s | 18H |
| 2.26 | m | 2H |
| 2.11 | m | 1H |
| 1.98 | m | 1H |

Optical rotation: $\alpha^{20D}$ + 1.14° (c = 1 $H_2O$)

Example 5

Preparation of 5-methyl-(6S)-tetrahydrofolic acid di L-arginine salt 10.0 g (17.67 mmol) of calcium levomefolate×3.8 hydrate under argon was suspended in 100 ml water at 70° C. Then 2.23 g (17.67 mmol) oxalic acid di-hydrate was added, followed by 6.15 g (35.33 mmol) L-arginine. After cooling to 0° C., the precipitated calcium oxalate was filtered off through a Hyflo pad and the resulting clear solution (pH 6) evaporated to dryness. The crude product was then thoroughly digested with methanol, filtered and dried under vacuum at 60° C., to give 13.98 g of the title compound. Analytical data:

| δ (1H) in ppm | Multiplicity | Intensity |
|---|---|---|
| 7.62 | d | 2H |
| 6.70 | d | 2H |
| 4.27 | m | 1H |
| 3.72 | t | 2H |
| 3.48 | m | 1H |
| 3.28 | m | 1H |
| 3.18 | t | 4H |
| 3.15 | m | 1H |
| 3.07 | m | 1H |
| 2.98 | m | 1H |
| 2.53 | s | 3H |
| 2.28 | m | 2H |
| 2.12 | m | 1H |
| 1.99 | m | 1H |
| 1.86 | m | 4H |
| 1.64 | m | 4H |

Optical rotation: $\alpha^{20D}$ + 30.0° (c = 1 $H_2O$)

Example 6

Preparation of 5-methyl-(6S)-tetrahydrofolic acid di-metformin salt 1.49 g (2.63 mmol) of calcium levomefolate×3.8 hydrate under argon was suspended in 38 ml water at 70° C. Then 0.332 g (2.63 mmol) oxalic acid di-hydrate dissolved in water was added, followed by 0.68 g (5.26 mmol) metformin free base dissolved in water. After cooling to 0° C., the precipitated calcium oxalate was filtered off through a Hyflo pad and the resulting clear solution (pH 6) evaporated to dryness. The crude product was then thoroughly digested with acetonitrile, filtered and dried under vacuum at 60° C., to give 1.89 g of the title compound. Analytical data:

| δ (1H) in ppm | Multiplicity | Intensity |
|---|---|---|
| 7.59 | d | 2H |
| 6.67 | d | 2H |
| 4.25 | m | 1H |
| 3.44 | m | 1H |
| 3.24 | m | 1H |
| 3.10 | m | 1H |
| 3.01 | m | 1H |
| 2.95 | s | 12H |
| 2.92 | m | 1H |
| 2.48 | s | 3H |
| 2.25 | m | 2H |
| 2.10 | m | 1H |
| 1.97 | m | 1H |

Optical rotation: $\alpha^{20D}$ + 17.95° (c = 1 $H_2O$)

Example 7

Preparation of 5-methyl-(6S)-tetrahydrofolic acid di phenformin salt 1.64 g (2.90 mmol) of calcium levomefolate×3.8 hydrate under argon was suspended in 35 ml Water at 70° C. Then 0.366 g (2.90 mmol) oxalic acid di-hydrate dissolved in water was added, followed by 0.68 g (5.26 mmol) phenformin free base dissolved in water. After cooling to 0° C., the precipitated calcium oxalate was filtered off through a Hyflo pad and the resulting clear solution (pH 5.5) evaporated to dryness. The crude product was then thoroughly digested with acetonitrile, filtered and dried under vacuum at 60° C., to give 2.54 g of the title compound. Analytical data:

| δ (1H) in ppm | Multiplicity | Intensity |
|---|---|---|
| 7.58 | d | 2H |
| 7.29 | m | 4H |
| 7.21 | m | 6H |
| 6.65 | d | 2H |
| 4.24 | m | 1H |
| 3.44 | m | 1H |
| 3.40 | m | 4H |
| 3.24 | m | 1H |
| 3.10 | m | 1H |
| 3.01 | m | 1H |
| 2.91 | m | 1H |
| 2.78 | m | 4H |
| 2.49 | s | 3H |
| 2.24 | m | 2H |
| 2.09 | m | 1H |
| 1.96 | m | 1H |

Optical rotation: $\alpha^{20D}$ + 16.06° (c = 1 $H_2O$)

Example 8

Preparation of 5-Formyl-(6S)-tetrahydrofolic acid mono L-arginine salt 0.258 g (0.429 mmol) of calcium levofolinate pentahydrate under argon was dissolved in 6 ml water at 70°. Then 0.0747 g (0.429 mmol) L-arginine was added, followed by 0.05419 g (0.429 mmol) oxalic acid dihydrate dissolved in water. After cooling to rt, the precipitated calcium oxalate was filtered off through a Hyflo pad and the resulting clear solution (pH 4) evaporated to dryness. The crude product was then thoroughly digested with methanol, filtered and dried under vacuum at 60°, to give 0.274 g of the title compound. Analytical data:

| δ (1H) in ppm | Multiplicity | Intensity |
|---|---|---|
| 7.59 | d | 2H |
| 6.67 | d | 2H |
| 4.25 | m | 1H |
| 3.69 | t | 1H |
| 3.58 | m | 1H |
| 3.41 | m | 2H |
| 3.19 | m | 5H |
| 2.71 | s | 3H |
| 2.27 | m | 2H |
| 2.10 | m | 1H |
| 1.96 | m | 1H |
| 1.83 | m | 2H |
| 1.60 | m | 2H |

Optical rotation: $\alpha^{20D}$ + 0.62° (c = 1 $H_2O$)

Example 9

Preparation of 5-Form M-(6S)-tetrahydrofolic acid mono metformin salt 100.0 mg (0.2112 mmol) of levofolinic acid and 28.1 mg (0.2175 mmol) metformin free base were suspended under argon in 2 ml Water and 4 ml methanol. After 15' of stirring and ultrasonification, the resulting solution (pH 5) was evaporated to dryness. The crude product was then thoroughly digested with acetonitrile, filtered and dried under vacuum at 60°, to give 122 mg of the title compound. Analytical data:

| δ (1H) in ppm | Multiplicity | Intensity |
|---|---|---|
| 8.51/7.8 | s/s | 1H |
| 7.54/7.50 | d/d | 2H |
| 6.62/6.57 | d/d | 2H |
| 4.73 | m | 1H |
| 4.27 | m | 1H |
| 3.42 | m | 1H |
| 3.28 | m | 2H |
| 3.16 | m | 1H |
| 2.92 | s | 6H |
| 2.32 | m | 2H |
| 2.12 | m | 1H |
| 1.95 | m | 1H |

Optical rotation: $\alpha^{20D}$ − 15.3° (c = 1 $H_2O$)

Example 10

Preparation of 5-Formyl-(6S)-tetrahydrofolic acid mono phenformin salt 100.1 mg (0.2114 mmol) of levofolinic acid and 44.7 mg (0.2178 mmol) phenformin free base were suspended under argon in 4 ml water and 4 ml methanol. After 10' of stirring and ultrasonification, the resulting solution (pH 5) was evaporated to dryness. The crude product was then thoroughly digested with acetonitrile, filtered and dried under vacuum at 60°, to give 137 mg of the title compound. Analytical data:

| δ (1H) in ppm | Multiplicity | Intensity |
|---|---|---|
| 8.50/7.80 | s/s | 1H |
| 7.54/7.50 | d/d | 2H |
| 7.27 | m | 2H |
| 7.19 | m | 3H |

-continued

| δ (1H) in ppm | Multiplicity | Intensity |
|---|---|---|
| 6.62/6.57 | d/d | 2H |
| 4.75 | m | 1H |
| 4.29 | m | 1H |
| 3.40 | m | 1H |
| 3.38 | m | 2H |
| 3.26 | m | 2H |
| 3.15 | m | 1H |
| 2.76 | m | 2H |
| 2.33 | m | 2H |
| 2.13 | m | 1H |
| 1.96 | m | 1H |

Optical rotation: $\alpha^{20D}$ + 13.50° (c = 1 $H_2O$)

Example 11

Preparation of 5-Formyl-(6S)-tetrahydrofolic acid mono choline salt 100.0 mg (0.2112 mmol) of levofolinic acid and 62.5 ul (0.2218 mmol) of a 45% methanolic solution of choline hydroxide were suspended under Argon in 2 ml Water and 4 ml Methanol. After 5' of stirring, ultrasonification and heating to reflux, the resulting slightly turbid solution (pH 5) was filtered still warm through a syringe filter and evaporated to dryness. The crude product was then thoroughly digested with acetonitrile, filtered and dried under vacuum at 60°, to give 118 mg of the title compound. Analytical data:

| δ (1H) in ppm | Multiplicity | Intensity |
|---|---|---|
| 8.50/7.80 | s/s | 1H |
| 7.54/7.50 | d/d | 2H |
| 6.62/6.57 | d/d | 2H |
| 4.73 | m | 1H |
| 4.27 | m | 1H |
| 3.93 | m | 2H |
| 3.43 | m | 1H |
| 3.39 | m | 2H |
| 3.27 | m | 2H |
| 3.16 | m | 1H |
| 3.07 | s | 9H |
| 2.32 | m | 2H |
| 2.12 | m | 1H |
| 1.95 | m | 1H |

Optical rotation: $\alpha^{20D}$ − 16.3° (c = 1 $H_2O$)

Example 12

Preparation of 5-Methyl-(6S)-tetrahydrofolic acid mono metformin salt 72.7 mg (0.1582 mmol) of Levomefolic acid and 21.5 mg (0.1661 mmol) Metformin free base were suspended under Argon in 10 ml Water and 20 ml Methanol. After stirring, ultrasonification and refluxing, the resulting solution was evaporated to dryness. The crude product was then thoroughly digested with Acetonitrile, filtered and dried under vacuum at 50°, to give 94.6 mg of the title compound. Analytical data:

| δ (1H) in ppm | Multiplicity | Intensity |
|---|---|---|
| 7.59 | d | 2H |
| 6.67 | d | 2H |
| 4.25 | m | 1H |
| 3.57 | m | 1H |
| 3.38 | m | 2H |
| 3.20 | m | 1H |
| 3.13 | m | 1H |
| 2.95 | s | 6H |
| 2.84 | m | 1H |
| 2.67 | s | 3H |
| 2.26 | m | 2H |
| 2.10 | m | 1H |
| 1.96 | m | 1H |

Example 13

Preparation of 5-Methyl-(6S)-tetrahydrofolic acid mono phenformin salt 90.4 mg (0.1967 mmol) of levomefolic acid and 42.4 mg (0.2066 mmol) phenformin free base were suspended under argon in 5 ml water and 10 ml methanol. After stirring, ultrasonification and refluxing for some time, the resulting solution was evaporated to dryness. The crude product was then thoroughly digested with acetonitrile, filtered and dried under vacuum at 50°, to give 133 mg of the title compound. Analytical data:

| δ (1H) in ppm | Multiplicity | Intensity |
|---|---|---|
| 7.56 | d | 2H |
| 7.27 | m | 2H |
| 7.19 | m | 3H |
| 6.63 | d | 2H |
| 4.23 | m | 1H |
| 3.53 | m | 1H |
| 3.38 | m | 2H |
| 3.35 | m | 2H |
| 3.12 | m | 1H |
| 3.07 | m | 1H |
| 2.76 | m | 2H |
| 2.64 | s | 3H |
| 2.25 | m | 2H |
| 2.09 | m | 1H |
| 1.96 | m | 1H |

Optical rotation: $\alpha^{20D}$ − 5.90° (c = 0.235 $H_2O$)

Example 14

Preparation of 5-Methyl-(6S)-tetrahydrofolic acid mono choline salt 2.61 g (4.611 mmol) of calcium levomefolinate×3.8hydrate under argon was suspended in 60 ml water at 95°. Then a filtered, aqueous solution of 568 mg (4.611 mmol) choline fluoride (obtained from choline chloride and silver fluoride) was added. Stirring was continued for 10' at 95° and after cooling to RT, the precipitated calcium fluoride was filtered off through a Hyflo pad and the resulting clear solution (pH 6.5) evaporated to dryness to give 2.568 g of the title compound. The crude product was thoroughly digested with Ethanol at 50°, then cooled in an ice-bath and filtered, dried under vacuum at 60°, to give 1.67 g of the title compound. Analytical data:

| δ (1H) in ppm | Multiplicity | Intensity |
|---|---|---|
| 7.56 | d | 2H |
| 6.65 | d | 2H |
| 4.20 | m | 1H |
| 3.95 | m | 2H |
| 3.43 | m | 1H |
| 3.40 | t | 2H |
| 3.20 | d | 1H |
| 3.08 | s | 9H |
| 3.04 | m | 1H |
| 2.99 | m | 1H |
| 2.89 | m | 1H |
| 2.42 | s | 3H |
| 2.20 | m | 2H |
| 2.04 | m | 1H |
| 1.91 | m | 1H |

Optical rotation: $\alpha^{20D}$ + 0.1° (c = 1 $H_2O$)

Example 15

Preparation of 5-Formyl-(6S)-tetrahydrofolic acid di acetylcholine salt 330.6 mg (0.5496 mmol) of calcium levofolinat pentahydrat under argon was dissolved in 6 ml water at 70°. Then a filtered, aqueous solution of 181.6 mg (1.099 mmol) acetylcholine fluoride (obtained from acetylcholine chloride and silver fluoride) was added at 30°. After cooling to 0°, the precipitated calcium fluoride was filtered off through a syringe filter and the resulting clear solution (pH 6) evaporated to dryness to give 407 mg of the title compound. Analytical data:

| δ (1H) in ppm | Multiplicity | Intensity |
|---|---|---|
| 8.52/7.81 | s/s | 1H |
| 7.56/7.59 | d/d | 2H |
| 6.64/6.58 | d/d | 2H |
| 4.75 | m | 1H |
| 4.42 | m | 4H |
| 4.20 | m | 1H |
| 3.61 | m | 4H |
| 3.45 | m | 1H |
| 3.30 | m | 2H |
| 3.18 | m | 1H |
| 3.09 | s | 18H |
| 2.20 | m | 2H |
| 2.05 | m | 1H |
| 2.02 | s | 6H |
| 1.91 | m | 1H |

Optical rotation: $\alpha^{20D}$ − 3.4° (c = 1 $H_2O$)

Example 16

Preparation of 5-Methyl-(6S)-tetrahydrofolic acid di acetylcholine salt 331.8 mg (0.5862 mmol) of calcium levomefolinate× 3.8hydrate under argon was suspended in 8 ml water at 70°. Then a filtered, aqueous solution of 193.6 mg (1.172 mmol) acetylcholine fluoride (obtained from acetylcholine chloride and silver fluoride) was added at 50°. After cooling to 0°, the precipitated calcium fluoride was filtered off through a syringe filter and the resulting clear solution (pH 6.5) evaporated to dryness to give 433 mg of the title compound. Analytical data:

| δ (1H) in ppm | Multiplicity | Intensity |
|---|---|---|
| 7.55 | d | 2H |
| 6.64 | d | 2H |
| 4.42 | m | 4H |
| 4.19 | m | 1H |
| 3.60 | m | 4H |
| 3.40 | m | 1H |
| 3.19 | m | 1H |
| 3.09 | s | 18H |
| 3.02 | m | 1H |
| 2.96 | m | 1H |
| 2.87 | m | 1H |
| 2.42 | s | 3H |
| 2.19 | m | 2H |
| 2.05 | m | 1H |
| 2.02 | s | 6H |
| 1.90 | m | 1H |

Optical rotation: $\alpha^{20D}$ 17.04° (c = 1 $H_2O$)

Example 17

Preparation of 5-Formyl-(6S)-tetrahydrofolic acid di betainmethylester salt 50.6 mg (0.0736 mmol) of silver levofolinate under argon was suspended in 2 ml water. Then a solution of 38.1 mg (0.1473 mmol) betain-methylester iodide in 1 ml water was added and the mixture heated under stirring to 90° C. After cooling down, the suspension was filtered through a syringe filter and the resulting clear solution evaporated, dried under vacuum at 50° C., to give 56 mg of the title compound. Analytical data:

| δ (1H) in ppm | Multiplicity | Intensity |
|---|---|---|
| 8.52/7.81 | s/s | 1H |
| 7.56/7.52 | d/d | 2H |
| 6.64/6.59 | d/d | 2H |
| 4.75 | m | 1H |
| 4.22 | s | 4H |
| 4.21 | m | 1H |
| 3.73 | s | 6H |
| 3.44 | m | 1H |
| 3.30 | m | 2H |
| 3.22 | s | 18H |
| 3.21 | m | 2H |
| 2.22 | m | 2H |
| 2.06 | m | 1H |
| 1.93 | m | 1H |

Example 18

Preparation of 5-Methyl-(6S)-tetrahydrofolic acid di betainmethylester salt 520.1 mg (0.919 mmol) of calcium levomefolinate× 3.8hydrate under argon was suspended in 6 ml Water at 70°. Then a filtered, aqueous solution of 291.8 mg (1.930 mmol) betain methylester fluoride (obtained from betain methylester iodide and silver fluoride) was added at 20°. After cooling to 0° C., the precipitated calcium fluoride was filtered off through a syringe filter and the resulting clear solution (pH 6.5) evaporated, dried under vacuum at 40°, to give 682 mg of the title compound. Analytical data:

| Optical rotation: $\alpha^{20D}$ + 10.5° (c = 1 $H_2O$) | | |
|---|---|---|
| δ (1H) in ppm | Multiplicity | Intensity |
| 7.56 | d | 2H |
| 6.64 | d | 2H |
| 4.22 | s | 4H |
| 4.20 | m | 1H |
| 3.73 | s | 6H |
| 3.42 | m | 1H |
| 3.23 | m | 1H |
| 3.21 | s | 18H |
| 3.08 | m | 1H |
| 3.00 | m | 1H |
| 2.90 | m | 1H |
| 2.46 | s | 3H |
| 2.20 | m | 2H |
| 2.05 | m | 1H |
| 1.92 | m | 1H |

Example 19

Preparation of 5-Formyl-(6S)-tetrahydrofolic acid di 2-dimethylaminoethanol salt 58.0 mg (0.1225 mmol) of levofolinic acid was suspended under argon in 0.5 ml water and treated with 24.7 μl (0.2450 mmol) of 2-dimethylaminoethanol (deanol). The mixture was stirred at room temperature (rt) until a clear solution is formed, evaporated and dried under vacuum at 45° C. to give 77 mg of the title compound. Analytical data:

| Optical rotation: $\alpha^{20D}$ − 8.5° (c = 1 $H_2O$) | | |
|---|---|---|
| δ (1H) in ppm | Multiplicity | Intensity |
| 8.50/7.80 | s/s | 1H |
| 7.54/7.51 | d/d | 2H |
| 6.62/6.57 | d/d | 2H |
| 4.73 | m | 1H |
| 4.18 | m | 1H |
| 3.75 | t | 4H |
| 3.43 | m | 1H |
| 3.28 | m | 2H |
| 3.17 | m | 1H |
| 3.11 | t | 4H |
| 2.75 | s | 12H |
| 2.18 | m | 2H |
| 2.03 | m | 1H |
| 1.90 | m | 1H |

Example 20

Preparation of 5-Formyl-(6S)-tetrahydrofolic acid mono 2-dimethylaminoethanol salt 71.6 mg (0.1512 mmol) of levofolinic acid was suspended under argon in 2 ml water and 5 ml methanol and treated with 15.7 μl (0.1558 mmol) of 2-dimethylaminoethanol (deanol). After ultrasonification and heating shortly to 60° C., a clear solution is formed (pH 5). This solution was evaporated and dried under vacuum at 45° C. to give 89.6 mg of the title compound. Analytical data:

| Optical rotation: $\alpha^{20D}$ − 13.8° (c = 1 $H_2O$) | | |
|---|---|---|
| δ (1H) in ppm | Multiplicity | Intensity |
| 8.58/7.87 | s/s | 1H |
| 7.61/7.57 | d/d | 2H |
| 6.69/6.64 | d/d | 2H |
| 4.81 | m | 1H |
| 4.33 | m | 1H |
| 3.85 | t | 2H |
| 3.50 | m | 1H |
| 3.34 | m | 2H |
| 3.24 | t | 2H |
| 3.22 | m | 1H |
| 2.87 | s | 6H |
| 2.38 | m | 2H |
| 2.17 | m | 1H |
| 2.01 | m | 1H |

Example 21

Preparation of 5-Methyl-(6S)-tetrahydrofolic acid mono L-arginine salt 82.0 mg (0.1785 mmol) of levomefolic acid was suspended under argon in 10 ml water and 20 ml methanol. 31.1 mg (0.1785 mmol) of L-arginine were added and the mixture treated until a solution was formed. This was evaporated, thoroughly digested with acetonitrile, filtered and dried under vacuum at 50° to give 109.7 mg of the title compound. Analytical data:

| δ (1H) in ppm | Multiplicity | Intensity |
|---|---|---|
| 7.59 | d | 2H |
| 6.67 | d | 2H |
| 4.25 | m | 1H |
| 3.69 | t | 1H |
| 3.58 | m | 1H |
| 3.41 | m | 2H |
| 3.19 | m | 5H |
| 2.71 | s | 3H |
| 2.27 | m | 2H |
| 2.10 | m | 1H |
| 1.96 | m | 1H |
| 1.83 | m | 2H |
| 1.60 | m | 2H |

Example 22

Preparation of 5-Formyl-(6S)-tetrahydrofolic acid mono acetylcholine salt 656.0 mg (1.090 mmol) of Calcium levofolinat pentahydrat under argon was dissolved in 10 ml water at 70°. Then a filtered, aqueous solution of 180.1 mg (1.090 mmol) acetylcholine fluoride (obtained from acetylcholine chloride and silver fluoride) was added at 30°. After cooling to 0°, the precipitated calcium fluoride was filtered off through a syringe filter and the resulting clear solution (pH 6) evaporated to dryness. The crude product was then thoroughly digested with acetonitrile, filtered and dried under vacuum at 50° C., to give 640 mg of the title compound. Analytical data:

| Optical rotation: $\alpha^{20D}$ − 7.7° (c = 1 $H_2O$) | | |
|---|---|---|
| δ (1H) in ppm | Multiplicity | Intensity |
| 8.58/7.86 | s/s | 1H |
| 7.61/7.58 | d/d | 2H |
| 6.69/6.64 | d/d | 2H |
| 4.81 | m | 1H |
| 4.49 | m | 2H |
| 4.26 | m | 1H |
| 3.67 | m | 2H |
| 3.50 | m | 1H |
| 3.57 | m | 2H |
| 3.25 | m | 1H |
| 3.15 | s | 9H |
| 2.25 | m | 2H |
| 2.10 | m | 1H |
| 2.08 | s | 3H |
| 1.97 | m | 1H |

Example 23

Preparation of 5-Methyl-(6S)-tetrahydrofolic acid mono acetylcholine salt 625.6 mg (1.105 mmol) of calcium levomefolinate× 3.8hydrate under argon was suspended in 12 ml water at 70°. Then a filtered, aqueous solution of 182.6 mg (1.105 mmol) acetylcholine fluoride (obtained from acetylcholine chloride and silver fluoride) was added at 30°. After heating the mixture shortly to 60° C. and cooling again to 20° C., the precipitated calcium fluoride was filtered off through a syringe filter and the resulting clear solution (pH 6) evaporated to dryness. The crude product was then thoroughly digested with acetonitrile, filtered and dried under vacuum at 50° C., to give 637 mg of the title compound. Analytical data:

-continued

| Optical rotation: $\alpha^{20D}$ + 29.7° (c = 1 $H_2O$) | | |
|---|---|---|
| δ (1H) in ppm | Multiplicity | Intensity |
| 7.61 | d | 2H |
| 6.69 | d | 2H |
| 4.48 | m | 2H |
| 4.26 | m | 1H |
| 3.66 | m | 2H |
| 3.45 | dd | 1H |
| 3.25 | m | 1H |
| 3.15 | s | 9H |
| 3.09 | m | 1H |
| 3.03 | m | 1H |
| 2.93 | m | 1H |
| 2.48 | s | 3H |
| 2.25 | m | 2H |
| 2.11 | m | 1H |
| 2.08 | s | 3H |
| 1.97 | m | 1H |

Solubility determination of selected folate salts was in general performed as follows:

A quantity of the salt corresponding to the expected solubility (between 1-100 mg) was provided and mixed with increments of the respective solvent until a solution was formed. This may require longer times, especially with highly soluble salts where solutions of extreme viscosity resulted.

The solubility in glycerol of the two di-arginine salts of 5-formyl-(6S)-tetrahydrofolic acid and 5-methyl-(6S)-tetrahydrofolic acid were subjected to a more detailed testing. The di-arginine salts were first finely ground in the agate mortar and then mixed with glycerine (50 mg in 1 ml solvent (5% m/v), under argon) and stirred with magnetic stirrer. After stirring overnight, a clear solution was achieved. After the 5% (m/v) solubility had already been confirmed, the same procedure was carried out at double concentration, resulting in solutions. Even at a concentration of 20% (m/v), the resulting solutions are very viscous.

For comparison, the solubility of the calcium salt of 5-methyl-(6S)-tetrahydrofolic acid (Gelpell) in glycerine was performed. The salt was clearly insoluble at 5% (m/v), 2.5% (m/v) and 1.6% (m/v). At 1.25% (m/v) a solution was achieved, slightly milky at the beginning, but after stirring it was clearly solved over the weekend. This confirms the previous data of approximately 1% solubility of this calcium salt.

Solubility of arginine (pestled) in glycerine: 100 mg in 500 μl, well soluble, 200 mg in 500 μl gives a solution after stirring overnight, a clear solution resulted after 36 h. (Quality glycerine: 99.5%, assay 99.99%, water but not specified. (Density: 1.26 g/ml))

All solubility data are indicated in mass-% (m/m); solubility was determined at 20° C.:

| Folate | Counter ion | Glycerine % | MeOH % | EtOH % | n-PrOH % | i-PrOH % | DMSO % |
|---|---|---|---|---|---|---|---|
| FTHF | di arginine | 19.23 | 0.06 | 0.06 | 0.06 | 0.06 | 0.25 |
| FTHF | di metformin | 7.35 | 55.80 | 0.63 | 0.62 | 0.63 | 0.25 |
| FTHF | di choline | 28.41 | >>50 | >50 | 0.31 | 0.32 | 0.25 |
| FTHF | di acetylcholine | 24.10 | 55.80 | 55.80 | 55.90 | 0.50 | 0.25 |
| FTHF | di deanol | 0.79 | 55.80 | 0.63 | 0.31 | 0.32 | 0.25 |
| MTHF | di arginine | 19.23 | 0.06 | 0.06 | 0.06 | 0.06 | 19.23 |
| MTHF | di metformin | 7.35 | 55.80 | 0.63 | 0.62 | 0.63 | 31.25 |
| MTHF | di acetylcholine | 24.10 | >>50 | 50.00 | 50.00 | 50.00 | 47.62 |
| Relative Polarity | | 0.812 | 0.762 | 0.654 | 0.617 | 0.546 | 0.444 |

Relative polarity data source: NIST site: http://webbook.nist.gov/chemistry/

FTHF = 5-Formyl-(6S)-tetrahydrofolic acid

MTHF = 5-Methyl-(6S)-tetrahydrofolic acid

Quantitative HPLC Measurements (20.00 mg Substance Dissolved in 10.00 ml $H_2O$, Amount Injected 1.0 µl, at 280 nm)

| Compound | theoretical content in titer | found | % of theoretical value | solvent content | including solvent |
|---|---|---|---|---|---|
| Ca-FTHF × 5H2O (titer) | 100% | — | 100% | — | — |
| FTHF × mono arginine | 92.89% | 92.79% | 99.89% | <0.1% MeOH | 99.89% |
| FTHF × di arginine | 73.20% | 69.00% | 94.26% | 3.7% MeOH | 98.00% |
| FTHF × mono metformin | 99.83% | 99.58% | 99.75% | 0.29% AcN | 100.04% |
| FTHF × di metformin | 82.21% | 75.78% | 92.18% | 8.0% EtOH | 100.18% |
| FTHF × mono phenformin | 88.64% | 90.18% | 101.74% | <0.1% AcN | 101.74% |
| FTHF × di phenformin | 68.05% | 66.94% | 98.37% | 4.0% AcN | 102.37% |
| FTHF × mono cholin | 104.33% | 98.44% | 94.36% | 3.59% AcN | 97.95% |
| FTHF × di cholin | 88.50% | 89.31% | 100.9% | 0% AcN; H2O | 100.9% |
| FTHF × mono acetylcholine | 97.24% | 93.45% | 96.10% | AcN; H2O | — |
| FTHF × di acetylcholine | 78.76% | 68.31% | 86.73% | AcN; H2O | — |
| FTHF × mono deanol | 106.93% | 100.05% | 93.56% | H2O | — |
| FTHF × di deanol | 92.31% | 91.84% | 99.48% | H2O | 99.48% |
| Ca-MTHF × 3.8H2O (titer) | 100% | — | 100% | — | — |
| MTHF × mono arginine | 89.32% | 81.12% | 90.82% | AcN; H2O | — |
| MTHF × di arginine | 70.06% | 67.41% | 96.22% | 2.3% MeOH | 98.52% |
| MTHF × mono metformin | 96.15% | 79.65% | 82.84% | 1.17% AcN | 85.01% |
| MTHF × di metformin | 78.85% | 74.38% | 94.33% | 0.2% AcN; H2O? | 94.53% |
| MTHF × mono phenformin | 85.14% | 68.57% | 80.54% | 3.86% AcN | 84.40% |
| MTHF × di phenformin | 65.06% | 63.43% | 97.49% | 0.47% AcN | 97.96% |
| MTHF × mono choline | 100.60% | 85.72% | 85.22% | 1.08% EtOH | 86.30% |
| MTHF × di cholin | 85.01% | 73.39%/ 80.51% | 86.33%/94.71% | H2O; <0.1% n-PrOH | 86.33%/94.71% |
| MTHF × mono acetylcholine | 93.60% | 80.13% | 85.61% | AcN; H2O | — |
| MTHF × di acetylcholine | 75.48% | 55.43% | 73.44% | H2O | — |
| MTHF × mono deanol | 103.17% | 102.58% | 99.43% | 0.3% IPOH | 99.73% |
| MTHF × di deanol | 88.75% | 81.62% | 91.97% | 0.67% n-PrOH; H2O | 92.64% |
| MTHF × di BetainOMe | 78.41% | 64.34% | 82.05% | H2O? | — |

Deanol = dimethylaminoethanol

What is claimed is:

1. An amorphous folate salt consisting of a tetrahydrofolic acid anion and an organic cation characterized in that the anion is selected from the group consisting of 10-formyl-(6R)-tetrahydrofolic acid, 5-methyl-(6S)-tetrahydrofolic acid, (6S)-tetrahydrofolic acid, 5, 10-Methylene-(6R)-tetrahydrofolic acid, and its oxidized derivatives JK12A and Mefox, and the cation is an organic compound selected from the group di-choline, di-acetylcholine, di-1,1-dimethyl-biguanidin, di-phenylethylbiguanidin, and di-betaine-methylester, wherein the folate salts have a high solubility in an apolar solvent, said apolar solvent having a relative polarity of 0.82 compared to water.

2. An amorphous folate acid salt according to claim 1, characterized in that the tetrahydrofolic acid anion is 5-methyl-(6S)-tetrahydrofolic acid and the organic cation is di-choline, wherein the $^1H$-NMR shifts in $D_2O$ are;

| δ (1H) in ppm | Multiplicity | Intensity |
|---|---|---|
| 7.60 | d | 2H |
| 6.68 | d | 2H |
| 4.24 | m | 1H |
| 3.98 | m | 4H |
| 3.44 | m | 1H |
| 3.43 | m | 4H |

-continued

| δ (1H) in ppm | Multiplicity | Intensity |
|---|---|---|
| 3.25 | m | 1H |
| 3.11 | s | 18H |
| 3.10 | m | 1H |
| 3.01 | m | 1H |
| 2.91 | m | 1H |
| 2.47 | s | 3H |
| 2.24 | m | 2H |
| 2.09 | m | 1H |
| 1.96 | m | 1H. |

3. An amorphous folate salt according to claim 1, characterized in that the tetrahydrofolic acid anion is 5-methyl-(6S)-tetrahydrofolic acid and the organic cation is di-(1,1-dimethyl-biguanidin), wherein the $^1H$-NMR shifts in $D_2O$ are:

| δ (1H) in ppm | Multiplicity | Intensity |
|---|---|---|
| 7.59 | d | 2H |
| 6.67 | d | 2H |
| 4.25 | m | 1H |
| 3.44 | m | 1H |
| 3.24 | m | 1H |

-continued

| δ (1H) in ppm | Multiplicity | Intensity |
|---|---|---|
| 3.10 | m | 1H |
| 3.01 | m | 1H |
| 2.95 | s | 12H |
| 2.92 | m | 1H |
| 2.48 | s | 3H |
| 2.25 | m | 2H |
| 2.10 | m | 1H |
| 1.97 | m | 1H. |

4. An amorphous folate acid salt according to claim 1, characterized in that the tetrahydrofolic acid anion is 5-methyl-(6S)-tetrahydrofolic acid and the organic cation is di-(phenylethyl-biguanidin), wherein the $^1$H-NMR shifts in $D_2O$ are:

| δ (1H) in ppm | Multiplicity | Intensity |
|---|---|---|
| 7.58 | d | 2H |
| 7.29 | m | 4H |
| 7.21 | m | 6H |
| 6.65 | d | 2H |
| 4.24 | m | 1H |
| 3.44 | m | 1H |
| 3.40 | m | 4H |
| 3.24 | m | 1H |
| 3.10 | m | 1H |
| 3.01 | m | 1H |
| 2.91 | m | 1H |
| 2.78 | m | 4H |
| 2.49 | s | 3H |
| 2.24 | m | 2H |
| 2.09 | m | 1H |
| 1.96 | m | 1H. |

5. A pharmaceutical composition, comprising at least one folate salt according to claim 1, as a main active compound and at least a pharmaceutically acceptable excipient.

* * * * *